US009383347B2

(12) United States Patent
Marugame

(10) Patent No.: US 9,383,347 B2
(45) Date of Patent: Jul. 5, 2016

(54) PATHOLOGICAL DIAGNOSIS RESULTS ASSESSMENT SYSTEM, PATHOLOGICAL DIAGNOSIS RESULTS ASSESSMENT METHOD, AND PATHOLOGICAL DIAGNOSIS RESULTS ASSESSMENT DEVICE

(71) Applicant: NEC Corporation, Tokyo (JP)

(72) Inventor: Atsushi Marugame, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 14/395,166

(22) PCT Filed: Mar. 7, 2013

(86) PCT No.: PCT/JP2013/001451
§ 371 (c)(1),
(2) Date: Oct. 17, 2014

(87) PCT Pub. No.: WO2013/175683
PCT Pub. Date: Nov. 28, 2013

(65) Prior Publication Data
US 2015/0072371 A1 Mar. 12, 2015

(30) Foreign Application Priority Data
May 24, 2012 (JP) ................................ 2012-118726

(51) Int. Cl.
G06K 9/00 (2006.01)
G01N 33/483 (2006.01)
(Continued)

(52) U.S. Cl.
CPC .......... *G01N 33/4833* (2013.01); *G06F 19/345* (2013.01); *G06F 19/3431* (2013.01);
(Continued)

(58) Field of Classification Search
USPC ......... 382/100, 103, 106–107, 128–134, 154, 382/155, 162–173, 181, 189–192, 199, 209, 382/219–220, 232, 254, 274, 276, 285–294, 382/305, 312; 435/287.1; 348/79; 250/201.3; 128/920
See application file for complete search history.

(56) References Cited

U.S. PATENT DOCUMENTS 6,091,842 A * 7/2000 Domanik ........... G01N 15/1468 250/201.3
6,148,096 A * 11/2000 Pressman .......... G01N 15/1468 348/79

(Continued)

FOREIGN PATENT DOCUMENTS

JP 2918663 7/1999
JP 2001-059842 3/2001
(Continued)

OTHER PUBLICATIONS

International Search Report PCT/JP2013/001451 dated Apr. 23, 2013.

Primary Examiner — Seyed Azarian
(74) Attorney, Agent, or Firm — Young & Thompson

(57) ABSTRACT

The pathological diagnosis results assessment system includes: a diagnosis unit to carry out pathological diagnosis of tissue specimen images, and generates diagnosis record information; a report storage unit to store reports in which pathological diagnosis results for the tissue specimen images are described; a report analysis unit to analyze the diagnosis results described in the reports stored in the report storage unit; and a report verification unit to compare the diagnosis result analyzed by the report analysis unit to the diagnosis record information, and determine a degree of matching on the diagnosis degree of the comparison result.

12 Claims, 10 Drawing Sheets

(51) Int. Cl.
*G06T 7/00* (2006.01)
*G06F 19/00* (2011.01)
*A61B 1/04* (2006.01)

(52) U.S. Cl.
CPC ..... *G06T7/0012* (2013.01); *G06T 2207/10024* (2013.01); *G06T 2207/10056* (2013.01); *G06T 2207/20081* (2013.01); *G06T 2207/20084* (2013.01); *G06T 2207/30024* (2013.01)

(56) References Cited

U.S. PATENT DOCUMENTS

| 6,430,309 | B1* | 8/2002 | Pressman | G01N 15/1468 |
| | | | | 128/920 |
| 2003/0215936 | A1* | 11/2003 | Kallioniemi | G01N 1/36 |
| | | | | 435/287.1 |
| 2007/0172100 | A1* | 7/2007 | Lefebvre | G01N 15/1475 |
| | | | | 382/128 |
| 2012/0327211 | A1* | 12/2012 | Yamamoto | G06F 19/366 |
| | | | | 348/79 |

FOREIGN PATENT DOCUMENTS

| JP | 3451307 | 9/2003 |
| JP | 3916395 | 5/2007 |
| JP | 2007-192821 | 8/2007 |
| JP | 2010-035756 | 2/2010 |
| JP | 2011-181015 | 9/2011 |
| JP | 2012-073179 | 4/2012 |
| WO | 2012157201 | 11/2012 |

* cited by examiner

Fig. 3A

| SPECIMEN ID | POSITION INFORMATION | DIAGNOSIS RESULT |
|---|---|---|
| 12345 | 4·8 | MALIGNANT |

Fig. 3B

| SPECIMEN ID | POSITION INFORMATION | DIAGNOSIS RESULT |
|---|---|---|
| 12345 | UPPER RIGHT | MALIGNANT |

Fig. 4

① PATIENT INFORMATION   *ID aaaaaaaa*
   AGE (BIRTH DATE)   *19450730*
   GENDER   *F*

② PATHOLOGIST INFORMATION
   NAME OF PATHOLOGIST   *TARO YAMADA*

③ SPECIMEN INFORMATION   *ID 12345*
   ACQUISITION DATE   *2011/10/05*
   NAME OF ORGAN   *STOMACH*
   POSITION IN ORGAN   *SUPPER PORTION*
   ACQUISITION METHOD (BIOPSY/OPERATION, etc)   *BIOPSY*

④ DIAGNOSIS INFORMATION
   DIAGNOSIS RESULT   *MALIGNANT:ADENOCARCINOMA*
                      *GROUP 5 (IN CASE OF STOMACH)*
   OBSERVATION:   *GLAND DUCTS OF DIFFERENT SIZES ARE CROWDED*

Fig. 5

| TISSUE SPECIMEN IDENTIFICATION INFORMATION (ID) | 12345 |
|---|---|
| REGION OF INTEREST | UPPER RIGHT |

Fig. 6

| BLOCK NUMBER | REGION OF INTEREST (ROI) |
|---|---|
| 3·4·8 | UPPER RIGHT |
| 1·2·5 | UPPER LEFT |
| 6·7·10·11 | MIDDLE, CENTER |

Fig. 9A

| ID | REGION OF INTEREST | NAME OF FEATURE AMOUNT | DENSITY OF FEATURE AMOUNT | SIZE VARIATION |
|---|---|---|---|---|
| 12345 | 4.8 | GLAND DUCTS | 70% (HIGH) | LARGE |

Fig. 9B

| ID | REGION OF INTEREST | NAME OF FEATURE AMOUNT | DENSITY OF FEATURE AMOUNT | SIZE VARIATION |
|---|---|---|---|---|
| 12345 | 4.8 | SIGNET RING CELLS | — | — |

Fig. 9C

| ID | REGION OF INTEREST | NAME OF FEATURE AMOUNT | AVERAGE OF ROUNDNESS | AVERAGE SIZE | SIZE VARIATION |
|---|---|---|---|---|---|
| 12345 | 4.8 | CELL NUCLEI | 0.4 (LOW) | MEDIUM | LARGE |

Fig. 10

| ID | REGION OF INTEREST | NAME OF FEATURE AMOUNT | DENSITY OF FEATURE AMOUNT | SIZE VARIATION |
|---|---|---|---|---|
| 12345 | UPPER PORTION | GLAND DUCTS | CROWDED | SIZES ARE DIFFERENT |

PATHOLOGICAL DIAGNOSIS RESULTS ASSESSMENT SYSTEM, PATHOLOGICAL DIAGNOSIS RESULTS ASSESSMENT METHOD, AND PATHOLOGICAL DIAGNOSIS RESULTS ASSESSMENT DEVICE

TECHNICAL FIELD

The present invention relates to a pathological diagnosis results assessment system, a pathological diagnosis results assessment method, and a pathological diagnosis results assessment device, for finding a deviation between a diagnosis result on a tissue specimen image and the contents of a report.

BACKGROUND ART

As a general pathological diagnosis method, there is known a method for observing and diagnosing a specimen (a pathological specimen) such as lesional tissues or cells obtained from a human body by placing the specimen on a glass slide and using a microscope. In recent years, other than the pathological diagnosis using a microscope, a pathological diagnosis (image diagnosis) is performed in such a manner that a specimen on a slide is read as a digital image using a scanner.

Normally, after a pathological diagnosis is performed using a microscope or a digital image, a pathologist summarizes a result on the pathological diagnosis as a pathological diagnosis report in writing. At the time of documentation, there may occur a deviation between the pathological diagnosis result and the contents of the pathological diagnosis report due to a mistake during office procedures or document mismanagement.

As a measure against the above problem, PTL 1 proposes a method, wherein detection is made as to which position and what feature in an image for medical diagnosis have been gazed, and how long the image has been gazed with use of detection of line of sight, and issued is a caution indicating that a region in need of special attention set in advance by a feature extraction may be overlooked. This method is effective in introducing a line of sight detection device in the field of diagnosis, and in a situation of issuing a caution.

CITATION LIST

Patent Literature

[PTL 1]: Japanese Patent Application Laid-Open No. 2010-035756

SUMMARY OF INVENTION

Technical Problem

Introduction of a line of sight detection device, however, may impose a burden on pathologists economically and/or psychologically, and the pathologists may feel reluctant to introduce the line of sight device. An object of the present invention is to prevent a deviation between a diagnosis result on a tissue specimen image and the contents of a report, and to reduce the risk of misdiagnosis, without using the introduction of a line of sight detection device.

Solution to Problem

To realize the above-mentioned object, a pathological diagnosis results assessment system of the present invention includes: a diagnosis unit to perform a pathological diagnosis of a tissue specimen image for generating diagnosis record information; a report storage unit to store a report describing a pathological diagnosis result on the tissue specimen image; a report analysis unit to analyze the diagnosis result described in the report stored in the report storage unit; and a report verification unit to compare the diagnosis result analyzed by the report analysis unit to the diagnosis record information, and determine a degree of matching on the diagnosis degree of the comparison result.

A pathological diagnosis results assessment method of the present invention includes: a diagnosing step of performing a pathological diagnosis of a tissue specimen image for generating diagnosis record information; a report storing step of storing a report describing a pathological diagnosis result on the tissue specimen image in a report storage unit; a report analyzing step of analyzing the diagnosis result described in the report stored in the report storage unit; and a report verifying step of comparing the diagnosis result analyzed in the report analyzing step to the diagnosis record information, and determining a degree of matching on the diagnosis degree of the comparison result.

A pathological diagnosis results assessment device of the present invention includes: a diagnosis unit to perform a pathological diagnosis of a tissue specimen image for generating diagnosis record information; a report storage unit to store a report describing a pathological diagnosis result on the tissue specimen image; a report analysis unit to analyze the diagnosis result described in the report stored in the report storage unit; and a report verification unit to compare the diagnosis result analyzed by the report analysis unit to the diagnosis record information, and determine a degree of matching on the diagnosis degree of the comparison result.

Advantageous Effects of Invention

According to the present invention, it is possible to prevent a deviation between a diagnosis result on a tissue specimen image and the contents of a report, and to reduce the risk of misdiagnosis.

BRIEF DESCRIPTION OF DRAWINGS

FIG. 3A is an explanatory diagram illustrating an example of diagnosis result information recorded in a diagnosis unit 102 in the first exemplary embodiment;

FIG. 3B is an explanatory diagram illustrating an example of diagnosis result information recorded in a report analysis unit 105 in the first exemplary embodiment;

FIG. 4 is an explanatory diagram illustrating an example of a pathological report stored in a report storage unit 104;

FIG. 5 is an explanatory diagram illustrating an example of dividing a tissue region into blocks;

FIG. 6 is an explanatory diagram illustrating an example of a mapping table between block numbers and regions of interest (ROI);

FIG. 9A is an explanatory diagram illustrating an example of diagnosis record information recorded in a diagnosis information storage unit 103;

FIG. 9B is an explanatory diagram illustrating an example of diagnosis record information recorded in the diagnosis information storage unit 103;

FIG. 9C is an explanatory diagram illustrating an example of diagnosis record information recorded in the diagnosis information storage unit 103;

FIG. 10 is an explanatory diagram illustrating an example of diagnosis record information recorded in a report analysis unit 105;

DESCRIPTION OF EMBODIMENTS

First Exemplary Embodiment

Figure 1:
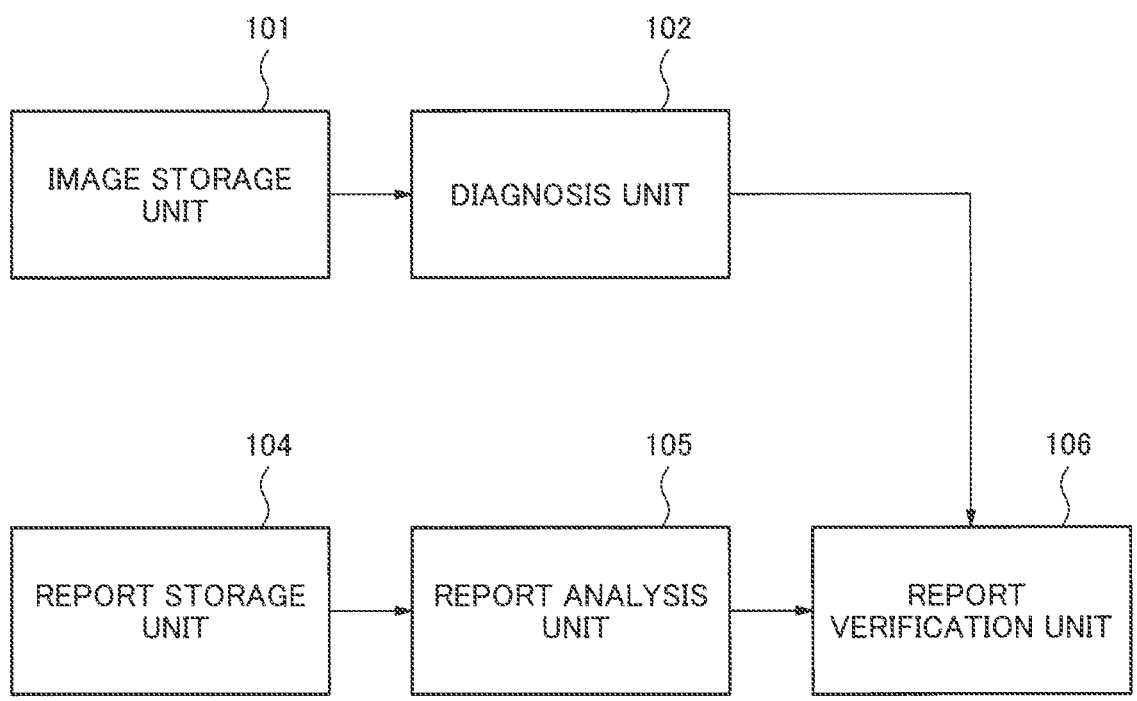
FIG. 1 is a block diagram illustrating a configuration example of a first exemplary embodiment of a pathological diagnosis assessment system according to the present invention.

In the following, exemplary embodiments of the present invention are illustratively described in details referring to the drawings. The constituent elements described in the following exemplary embodiments are merely exemplary elements, and do not limit the technical scope of the present invention.

FIG. 1 is a block diagram illustrating a configuration example of the first exemplary embodiment of a pathological diagnosis assessment system according to the present invention. An image storage unit 101 is configured to read a specimen slide of lesional tissues with use of an imaging device such as a scanner for storing the generated tissue specimen image.

A diagnosis unit 102 is configured to request the image storage unit 101 for transmission of a tissue specimen image to extract the contour of a tissue in the obtained tissue image. Further, the diagnosis unit 102 has a function of extracting various features residing in the tissue. Examples of the features for use in pathological diagnosis are nuclei, gland ducts, signet ring cells, mucus, necrotic cells, and the like.

Further, the diagnosis unit 102 is configured to define a rough region including a target region using the color value of pixels, and thereafter, to extract a feature region from the target region with use of general image processing means such as an edge extraction filter or a template matching. The feature region is a region including features to be used in pathological diagnosis.

Further, the diagnosis unit 102 is configured to determine and analyze a region of interest (ROI) on the basis of various features extracted from the tissue specimen image for performing pathological diagnosis. At the time of analysis, values (feature amounts) relating to the color, the shape, and the like of features are defined as feature vectors. The diagnosis unit 102 is configured to input the feature vectors to a discriminator that has learned in advance by a machine learning system such as a neural network (NN) or a support vector machine (SVM) for performing pathological diagnosis.

As illustrated in FIG. 3A, the obtained diagnosis result is stored in the diagnosis unit 102 along with tissue specimen identification information (ID) and a region of interest (ROI) as diagnosis record information. The tissue specimen identification information (ID) is information for identifying a tissue specimen. In the present exemplary embodiment, a tissue specimen is labeled with a barcode including identification information.

The ROI (Region Of Interest) is a target region for pathological diagnosis in a tissue specimen image including features that are important for pathological diagnosis. Further, the diagnosis result is a pathological diagnosis result on a tissue specimen. In the present exemplary embodiment, the diagnosis result indicates whether the tissue specimen is "malignant" or "benign".

A report storage unit 104 is configured to store pathological reports. Generally, as illustrated in FIG. 4, a pathological report describes text information such as patient information (tissue specimen identification information (ID), age, gender), pathologist information, specimen information (the name of an organ, a collecting position of biopsy in the organ, a collecting method), and diagnosis information (a diagnosis result, an observation). The pathological report may additionally include other items necessary for pathological diagnosis, as necessary.

A report analysis unit 105 is configured to extract a diagnosis result by syntax analysis using natural language processing, on the basis of the contents of a pathological report. The diagnosis result indicates whether the tissue specimen is "malignant" or "benign". As illustrated in FIG. 3B, the diagnosis result is stored in the report analysis unit 105 along with the tissue specimen identification information (ID) and the region of interest (ROI) as diagnosis record information.

A report verification unit 106 is configured to assess a degree of matching between the diagnosis result stored in the diagnosis unit 102 and the diagnosis record information stored in the report storage unit 104. In the first exemplary embodiment, the report verification unit 106 is configured to assess a degree of matching between the diagnosis record information stored in the diagnosis unit 102 and the diagnosis record information stored in the report storage unit 104.

Figure 2:
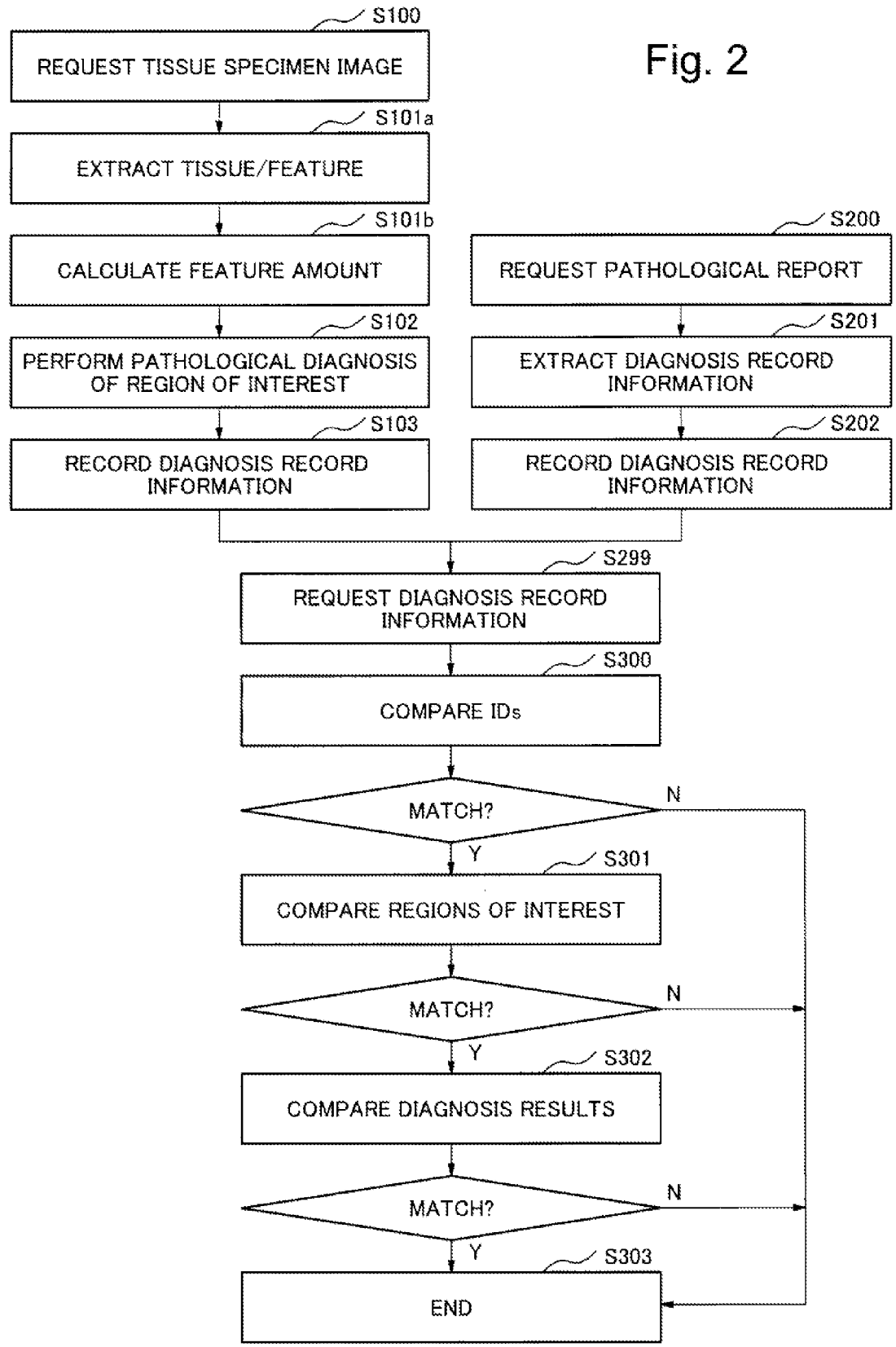
FIG. 2 is a flowchart illustrating an example of an operation sequence to be performed by the pathological diagnosis assessment system of the first exemplary embodiment.

FIG. 2 is a flowchart illustrating an example of an operation sequence to be performed by the pathological diagnosis assessment system in the first exemplary embodiment. The diagnosis unit 102 requests a tissue specimen image stored in the image storage unit 101 (in Step S100). The diagnosis unit 102 extracts the contour of a tissue in the requested tissue specimen image by the same method as the aforementioned feature extraction method. Further, the diagnosis unit 102 extracts various features residing in the tissue, and calculates feature amounts as attribute information (representing the density of a feature, the shape of a feature, the size of a feature, etc.) of various features (in Steps S101a and S101b).

The diagnosis unit 102 determines a region of interest (ROI) on the basis of the extracted various feature information for performing pathological, diagnosis (in Step S102). The diagnosis unit 102 may use the method described in Unexamined Japanese Patent Application Kokai Publication No. 2009-175040, or may use another method, as the method for determining a region of interest (ROI).

The diagnosis record information in the first exemplary embodiment is tissue specimen identification information (ID), and information relating to a region of interest (ROI) and a diagnosis result. The diagnosis information storage unit 103 stores the diagnosis record information obtained by the diagnosis unit 102 as a table as illustrated in FIG. 3A (in Step S103).

On the other hand, the report analysis unit 105 requests a report stored in the report storage unit 104 (in Step S200). The report analysis unit 105 extracts the diagnosis record information described in the report (in Step S201), and records the extracted diagnosis record information in the report analysis unit 105, as a table as illustrated in FIG. 3B (in Step S202).

The report verification unit 106 compares between the diagnosis record information (see FIG. 3A and FIG. 3B) recorded in the diagnosis unit 102 and in the report analysis unit 105, and assesses a degree of matching between both of the diagnosis record information. In the following, a flow of comparing between the diagnosis record information is described.

<Comparison of Tissue Specimen Identification Information (ID)>

First of all, the report verification unit 106 requests diagnosis record information from both the diagnosis unit 102 and the report analysis unit 105 (in step 299), then compares between the pieces of tissue specimen identification information (IDs) (in Step S300). When the pieces of tissue specimen identification information (IDs) match with each other, subsequently, the report verification unit 106 compares between the regions of interest (ROI) (in Step S301). When the pieces of tissue specimen identification information (IDs) do not match with each other, the flow is ended (in Step S303).

<Comparison of Regions of Interest>

When the pieces of tissue specimen identification information (IDs) match with each other in Step S300, subsequently, the report verification unit 106 compares between the regions of interest (ROI) (in Step S301). In the following, a flow of comparing between the regions of interest (ROI) is described.

As illustrated in FIG. 5, the report verification unit 106 sets a rectangular region (a bounding box) in contact with an upper end, a lower end, a left end, and a right end of the tissue region extracted by the diagnosis unit 102. The report verification unit 106 divides the inside of the rectangular region into a plurality of blocks. For instance, the report verification unit 106 generates sixteen blocks in total by dividing the rectangular region into four in a vertical direction and dividing the rectangular region into four in a horizontal direction, and assigns the numbers 1 to 16 to the respective blocks.

Mapping of position information between a pathological report and each of the blocks is performed as follows. It is often the case that information relating to a region of interest (ROI) described in a pathological report is indicated only by a rough position such as an "upper-right" position. Defining the mapping between regions of interest (ROI) and block numbers in advance as illustrated in FIG. 6 makes it possible to specify a correlation between a region of interest described in a pathological report and a region of interest in a tissue specimen image.

On the other hand, the report analysis unit 105 performs syntax analysis on the pathological report, and acquires region-of-interest (ROI) information. For instance, it is assumed that the word "upper right" is extracted as region-of-interest (ROI) information. In this example, the position in the tissue specimen image related to the "upper right" position in the pathological report is defined as the block numbers 3, 4, and 8 as illustrated in FIG. 6. Therefore, it is determined that both of the region-of-interest (ROI) information match with each other (in Step S301). When the regions of interest do not match with each other, the flow is ended (in Step S303).

<Comparison of Diagnosis Results>

Further, the report verification unit 106 compares between the diagnosis results recorded in the diagnosis unit 102 and in the report analysis unit 105 (in Step S302). When both of the diagnosis results match with each other in the word "benign", the report verification unit 106 determines that the final diagnosis result is "benign", and the flow is ended (in Step S303).

On the other hand, when both of the diagnosis results match with each other in the word "malignant", the report verification unit 106 determines that the final diagnosis result is "malignant", and the flow is ended (in Step S303). The report verification unit 106 may perform a detailed evaluation (e.g. grading) on cancerous malignancy. In the detailed evaluation, the report verification unit 106 may display diagnosis record information on a display screen.

Further, when both of the diagnosis results do not match with each other, the report verification unit 106 displays a caution on the display screen, and the flow is ended (in Step S303).

According to the first exemplary embodiment of the present invention, it is possible to prevent a deviation between a diagnosis result on a tissue specimen image and the contents of a report created by a pathologist.

Second Exemplary Embodiment

In the second exemplary embodiment, features and attribute information thereof necessary for pathological diagnosis are extracted on the basis of the contents of a pathological report stored in a report storage unit 104. Comparison is made between the features and between the attribute information thereof included in diagnosis record information stored in a diagnosis information storage unit 103, and a degree of matching between the features and between the attribute information is determined. Further, a score in accordance with the degree of matching therebetween is calculated. When the calculated score is deviated from a predetermined standard value by a predetermined value or more, a caution is displayed.

Figure 7:
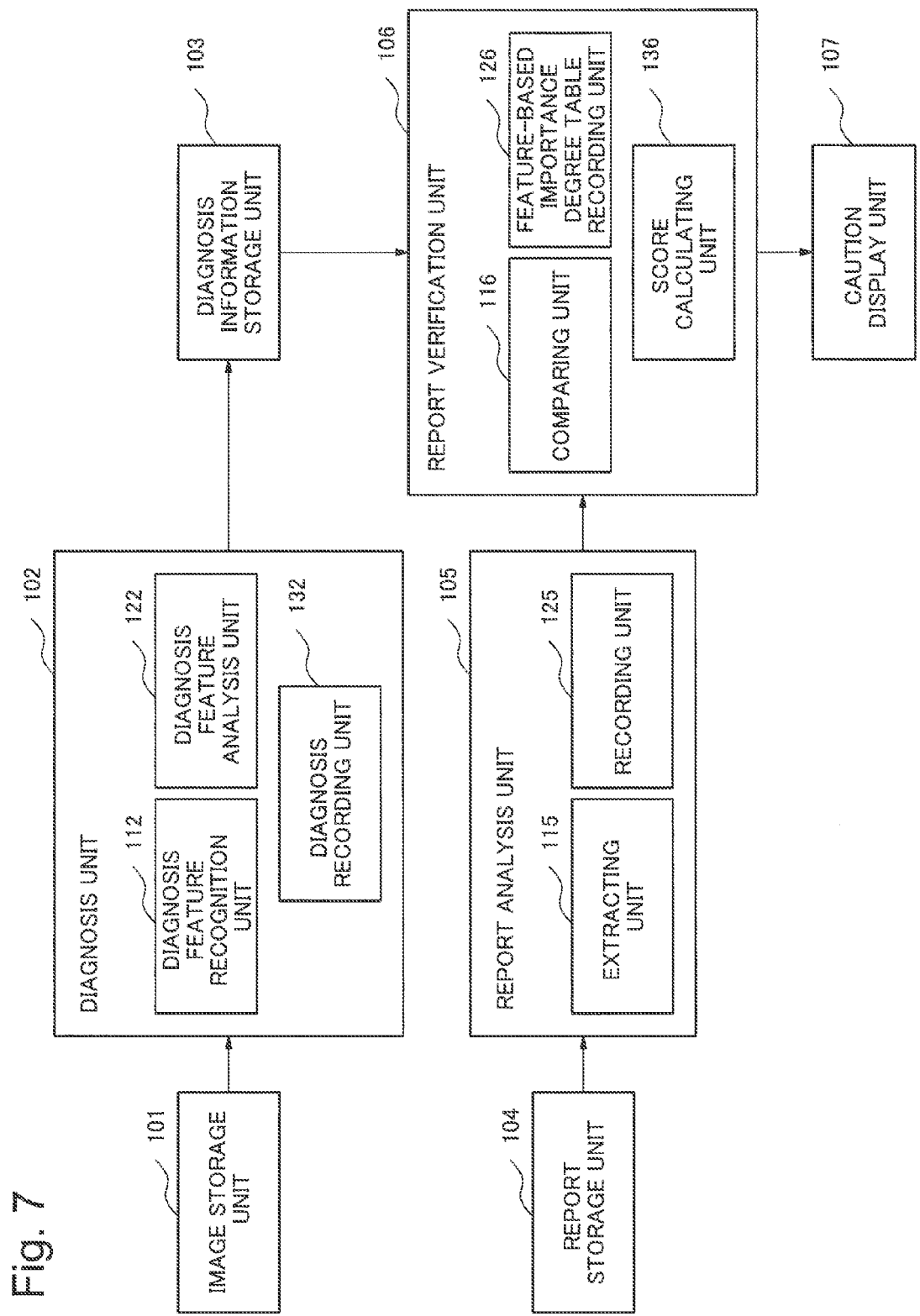
FIG. 7 is a block diagram illustrating a configuration example of a second exemplary embodiment of the pathological diagnosis assessment system according to the present invention.

FIG. 7 is a block diagram illustrating a configuration example of the second exemplary embodiment of the pathological diagnosis assessment system according to the present invention. A difference from the first exemplary embodiment is that a diagnosis unit 102 includes a diagnosis feature recognition unit 112 and a diagnosis feature analysis unit 122. A further difference from the first exemplary embodiment is that a report verification unit 106 includes a feature-based importance degree table recording unit 126, and a score calculating unit 136. Description on the configuration substantially the same as in the first exemplary embodiment is omitted.

The diagnosis unit 102 includes the diagnosis feature recognition unit 112, the diagnosis feature analysis unit 122, and a diagnosis recording unit 132.

The diagnosis feature recognition unit 112 is configured to request an image storage unit 101 for transmission of a tissue specimen image to extract the contour of a tissue in the obtained tissue image. Further, the diagnosis feature recognition unit 112 has a function of extracting various features residing in the tissue. Examples of the features for use in pathological diagnosis are nuclei, gland ducts, signet ring cells, mucus, necrotic cells, and the like. The feature extraction method is the same as in the first exemplary embodiment, and accordingly, description thereof is omitted herein.

The diagnosis feature analysis unit 122 is configured to analyze a tissue and features in the tissue image extracted by the diagnosis feature recognition unit 112 for performing pathological diagnosis.

The diagnosis feature analysis unit 122 is configured to extract a region serving as a feature from the tissue image. The diagnosis feature analysis unit 122 is configured to calculate, as the feature, an amount (an area; a circumferential length; a degree of roundness; a major axis, a minor axis, and a ratio between the major axis and the minor axis; the number of thinned pixels and a measuring line of the pixels; an endpoint; and the number of points of intersection) relating to the shape of the region, and an average value and dispersion of color elements (such as RGB, HSV) of pixels in the region. The diagnosis feature analysis unit 122 is configured to assess the degree of benignity or malignancy, with use of threshold value processing, or a machine learning method as represented by a neural network (NN), a support vector machine (SVM), or the like, using all these values as a feature amount vector.

The diagnosis feature analysis unit 122 may assess the degree by binary values such as 0 and 1. Further, the diagnosis feature analysis unit 122 may assess the degree, with use of a degree of deviation from a threshold value, or with use of consecutive values such as numerical values calculated by a machine learning method. The diagnosis feature analysis unit 122 may utilize a generally known technique of a feature analysis method including the above method.

The diagnosis recording unit 132 is configured to record tissue specimen identification information (ID), a region of interest (ROI), the name of a feature, and attribute information of the feature in the tissue specimen image analyzed by the diagnosis feature analysis unit 122 as diagnosis record information.

The report analysis unit 105 includes an extracting unit 115, and a recording unit 125.

The extracting unit 115 is configured to extract a feature and attribute information of the feature by syntax analysis of natural language processing, on the basis of the contents of a pathological report. The attribute information of a feature indicates the density of a feature, the shape of a feature, the size of a feature, and the like. The extracting unit 115 performs a pathological diagnosis on the basis of the obtained feature and the obtained attribute information of the feature. As illustrated in FIG. 10, the diagnosis result is stored in the diagnosis information storage unit 103 along with the tissue specimen identification information (ID) and the region of interest (ROI) as diagnosis record information.

The recording unit 125 is configured to record the feature and the attribute information thereof extracted by the extracting unit 115, as illustrated in FIG. 10.

The report verification unit 106 includes a comparing unit 116, the feature-based importance degree table recording unit 126, and the score calculating unit 136.

The comparing unit 116 is configured to compare between the diagnosis record information stored in the diagnosis information storage unit 103, and the feature and the attribute information thereof recorded in the recording unit 125 of the report analysis unit 105.

Figure 11:
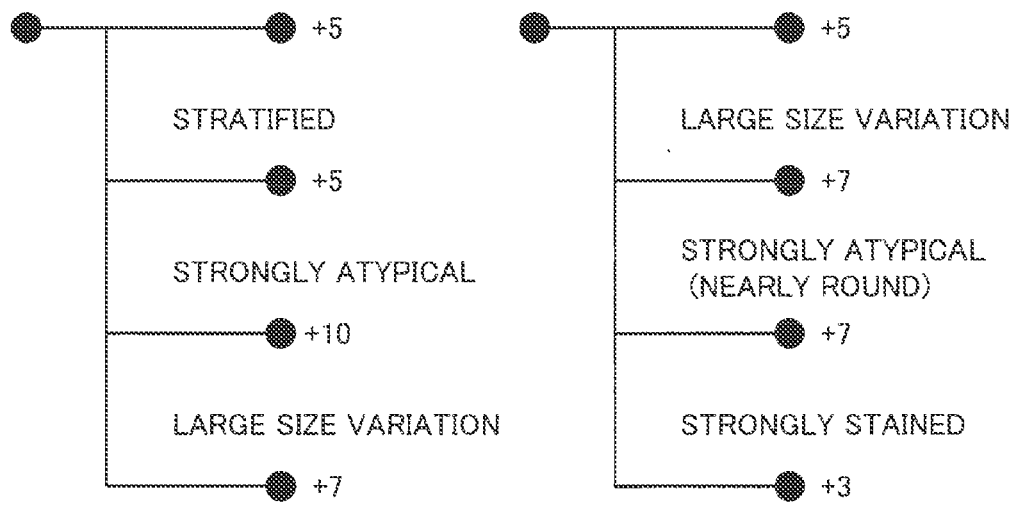
FIG. 11 is an explanatory diagram illustrating an example of various features and weighting values related to attribute information thereof.

The feature-based importance degree table recording unit 126 is configured to record a weighting value to be used in score calculation, as illustrated in FIG. 11. The weighting value is set in advance in relation to each of the feature and the attribute information thereof.

Specifically, the weighting value shows an extremely large value, for instance, in a signet ring cell in stomach cancer diagnosis or comedo necrosis in prostatic cancer diagnosis, in which malignancy determination is strongly supported on the basis of the presence or absence of the feature.

There is a feature, as represented by gland ducts, which cannot necessarily support malignancy determination solely by the feature. In this case, a weighting value is set in accordance with an incidence of malignancy or a severity (in case of cancer, the progress is fast and the like) using attribute information of the feature. For instance, when the feature is "gland ducts", attribute information of the feature includes the words that indicate the size, the density, the shape, and the like. For instance, it is assumed that a pathological report describes an observation "gland ducts of different sizes are crowded". In this case, as illustrated in FIG. 11, a weighting value +5 is set for the item "gland ducts are crowded", and a weighting value +7 is set for the item "the sizes of gland ducts differ from each other".

The score calculating unit 136 is configured to calculate a caution score by a weighted sum, for instance, with use of a matching score provided by the comparing unit 116, and the weighting values recorded in the feature-based importance degree table recording unit 126.

The matching score is a score to be provided by the degree of matching to be obtained when the features are compared with each other. Comparison is made between both of the features in the diagnosis record information of one tissue specimen image recorded in the diagnosis information recording unit 103, and recorded in the recording unit 125 of the report analysis unit 105. In this case, if the features match with each other, +1 is provided as the matching score, and if the features do not match with each other, −1 is provided as the matching score.

The caution score is a score to be derived by multiplying a matching score on features with a predetermined weighting value as illustrated in FIG. 11 with respect to an item in which the features or attribute information thereof match with each other, and summing the multiplication results. The caution score serves as an index indicating a degree of deviation between the pathological diagnosis results in the diagnosis information recording unit 103 and in the report analysis unit 105.

In the following description, as an example, there is described a case, in which a pathological diagnosis is performed with use of a tissue specimen suspected of having stomach cancer. Further, description is made based on the premise that a pathological diagnosis is performed with use of "gland ducts" as the feature, and "size, shape, density, etc." as the attribute information.

The diagnosis feature recognition unit 112 is configured to extract a tissue, and various feature regions in the tissue specimen image. Further, the diagnosis feature analysis unit 122 is configured to determine a region of interest (ROI) on the basis of the extracted various feature information for performing pathological diagnosis. The foregoing steps are the same as those in the first exemplary embodiment, and accordingly, description thereof is omitted.

Figure 12:
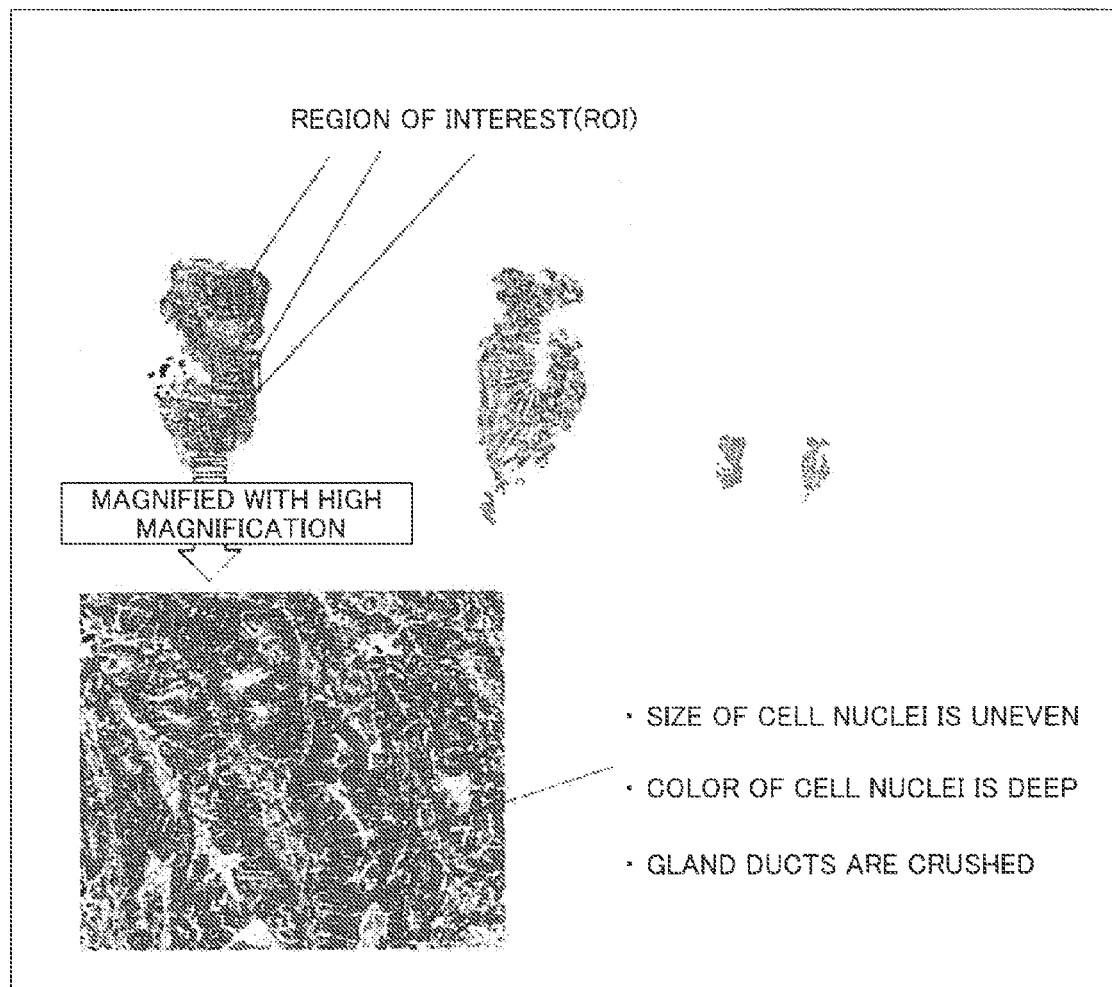
FIG. 12 is an explanatory diagram illustrating an example of observing a region of interest (ROI) with a high magnification.

FIG. 12 is an explanatory diagram illustrating that a plurality of regions of interest (ROI) are set on the basis of a tissue, and feature information in the tissue specimen image recognized by the diagnosis feature recognition unit 112, and one region of interest (ROI) is determined from among the regions of interest. When the region of interest (ROI) is determined, the diagnosis feature analysis unit 122 sets the feature residing in the region of interest to a magnification suitable for diagnosis. The pathological diagnosing method of a region of interest (ROI) to be performed by the diagnosis feature analysis unit 122 is the same as in the first exemplary embodiment, and accordingly, description thereof is omitted.

The diagnosis feature analysis unit 122 is configured to transmit, to the diagnosis information storage unit 103, the tissue specimen identification information (ID), the region-of-interest (ROI) information, the name of the feature, and the attribute information thereof acquired in analyzing the gland ducts. The diagnosis information storage unit 103 is configured to record the transmitted information, as illustrated in FIGS. 9A to 9C.

On the other hand, the report stored in the report storage unit 104 is transmitted to the report analysis unit 105. The extracting unit 115 of the report analysis unit 105 is configured to extract the pathological specimen identification information (ID), the region of interest (ROI), the name of the feature, and the attribute information thereof described in the report, and to record the extracted information in the recording unit 125 in the format of a table as illustrated in FIG. 10.

In the following, there is described a flow of extracting the name of a feature and attribute information thereof by the report analysis unit 105, on the basis of the contents of a report stored in the report storage unit 104. For instance, it is assumed that a pathological report includes an observation "gland ducts of different sizes are crowded". In this case, the report analysis unit 105 extracts "gland ducts" as a feature, and "sizes are different from each other" and "crowded" as attribute information of the feature. The obtained information is recorded in the recording unit 125 of the report analysis unit 105 in the format of a table as illustrated in FIG. 10.

Figure 8:
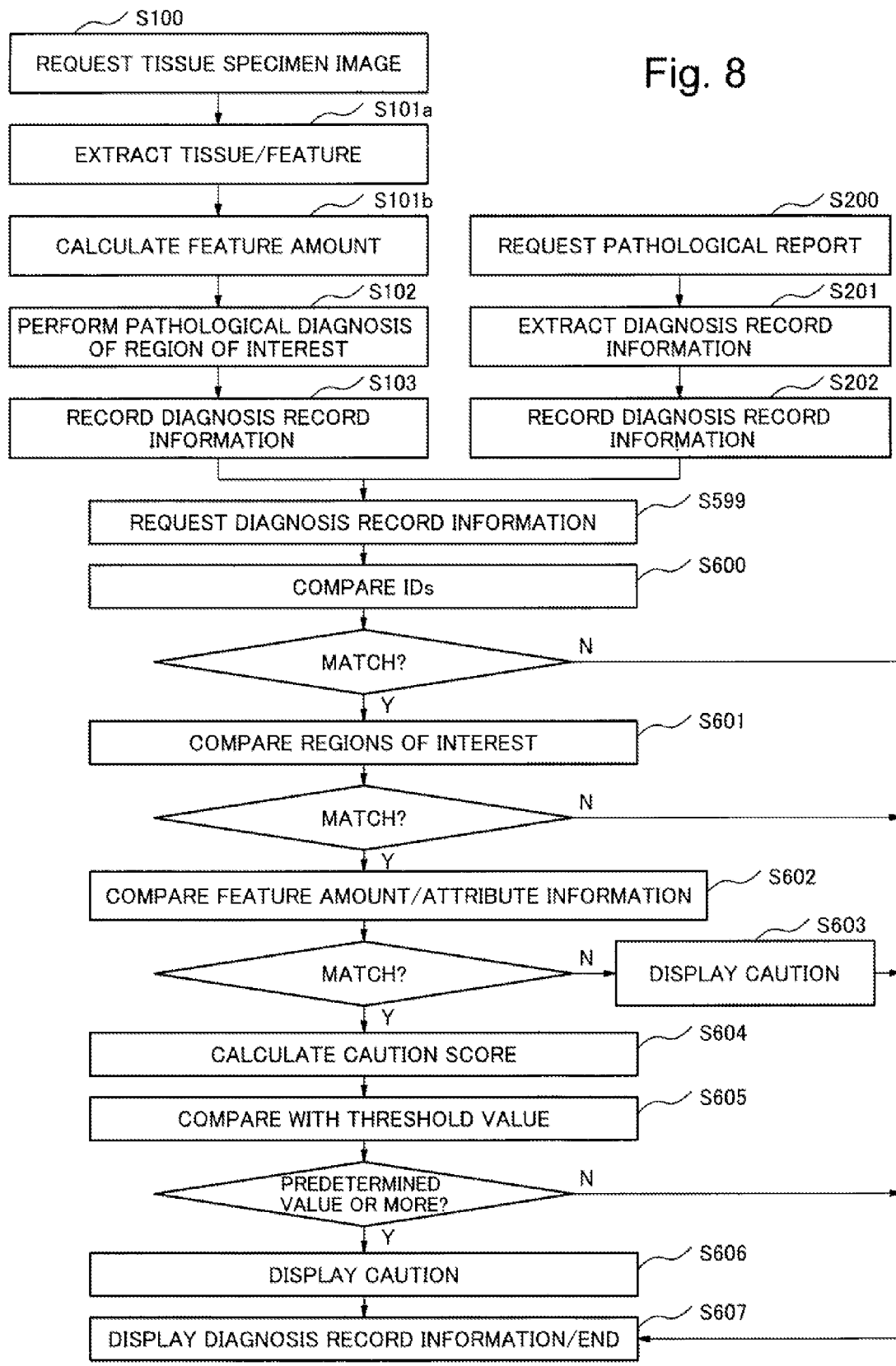
FIG. 8 is a flowchart illustrating an example of an operation sequence to be performed by the pathological diagnosis assessment results system of the second exemplary embodiment.

The comparing unit 116 of the report verification unit 106 is configured to compare between the diagnosis record information including a feature and attribute information thereof recorded in the recording unit 125, and the diagnosis record information stored in the diagnosis information storage unit 103, and to assess a degree of matching between both of the diagnosis record information. In the following, a flow of assessment processing is described referring to FIG. 8.

<Comparison of Tissue Specimen Identification Information (ID)>

The report verification unit 106 requests diagnosis record information from both the diagnosis information storage unit 103 and the report analysis unit 105 (in step 599), then compares between the tissue specimen identification information (ID) stored in the diagnosis information storage unit 103, and the tissue specimen identification information (ID) in the report analyzed by the report analysis unit 105 (in Step S600). When the pieces of tissue specimen identification information match with each other, subsequently, the report verification unit 106 compares between the regions of interest (ROI) (in Step S601). When the regions of interest (ROI) do not match with each other, the flow is ended (in Step S607).

<Comparison of Regions of Interest (ROI)>

The report verification unit 106 compares between the region of interest (ROI) in the diagnosis record information stored in the diagnosis information storage unit 103, and the region of interest (ROI) in the diagnosis record information in the report analyzed by the report analysis unit 105 (in Step S601). The comparing method is the same as in the first exemplary embodiment, and accordingly, description thereof is omitted.

<Comparison of Features and Attribute Information Thereof>

First of all, the comparing unit 116 of the report verification unit 106 compares between the feature in the information (see FIG. 9A) stored in the diagnosis information storage unit 103, and the feature stored in the report analysis unit 105, out of the feature and the attribute information thereof (see FIG. 10) (in Step S602). In the case of the present exemplary embodiment, both of the features are "gland ducts". Therefore, the comparing unit 116 determines that the features match with each other, and +1 is provided as a matching score on features.

Subsequently, the comparing unit 116 of the report verification unit 106 compares between attribute information of the feature recorded in the diagnosis information storage unit 103 and in the report analysis unit 105. A threshold value condition relating to the attribute information is set in advance in the report verification unit 106 for each description of the attribute information. The comparing unit 116 determines that both of the attribute information match with each other when the attribute information recorded in the diagnosis record information 103, and in the report analysis unit 105 satisfy the threshold value condition.

As an example of comparing between attribute information of a feature, there is described a case of comparing between information relating to a density. The diagnosis information storage unit 103 stores the information (see FIG. 9A) indicating "density: 70%". This indicates a ratio of gland ducts with respect to the entirety of the region of interest (ROI). On the other hand, the report analysis unit 105 stores the information (see FIG. 10) indicating "crowded".

In this case, both of the attribute information of a feature i.e., "density: 70%" and "crowded" satisfy a predetermined threshold value condition. Therefore, the report verification unit 106 determines that both of the attribute information match with each other.

Next, as an example of comparing between attribute information of a feature, there is described a case of comparing between information relating to the size of a feature. The diagnosis information storage unit 103 stores the information (see FIG. 9A) indicating "size variation: large". The report analysis unit 105 stores the information (see FIG. 10) indicating "sizes are different from each other". In this case, both of the attribute information satisfy a predetermined threshold value condition. Accordingly, the report verification unit 106 determines that both of the attribute information match with each other.

Further, the score calculating unit 136 of the report verification unit 106 derives a caution score by multiplying a matching score on each of features with a predetermined weighting value in the feature-based importance degree table recording unit 126 with respect to an item in which the features or attribute information match with each other, and summing the multiplication results (in Step S604).

In the present comparative example, the features are determined to match with each other by the word "gland ducts". Therefore, the matching score is set to be +1. Further, the item "sizes are different from each other" about gland ducts has a weighting value +7, and the item "crowded" about gland ducts has a weighting value +5, from the information recorded in the feature-based importance degree table recording unit 126.

The score calculating unit 136 derives a caution score by multiplying the matching score +1 obtained as described above with each of the two weighting values, and summing the multiplication results. In this example, the calculated caution score is +12. The score calculating unit 136 may add and/or subtract points to and/or from the calculated caution score, as necessary, according to the arrangement order of the features and the attribute information thereof in the report.

The caution score calculated by the score calculating unit 136 of the report verification unit 106 is transmitted to a caution display unit 107. The caution display unit 107 compares between a predetermined threshold value and the caution score transmitted from the report verification unit 106 (in Step S605).

When the caution score is deviated from the threshold value by a predetermined value or more, the caution display unit 107 displays a caution to the user (in Step S606), and ends the processing (in Step S607). When the caution score is not deviated from the threshold value by a predetermined value or more, the caution display unit 107 ends the processing as it is (in Step S607). In any of the cases, the caution display unit 107 may display a caution score concurrently with a caution display (in Step S607).

Subsequently, there is described processing to be performed when the feature in the diagnosis record information (see FIG. 9B) stored in the diagnosis information storage unit 103, and the feature in the diagnosis record information (see FIG. 10) recorded in the report analysis unit 105 do not match with each other.

First of all, the comparing unit 116 of the report verification unit 106 compares between the feature in the diagnosis record information (see FIG. 9B) stored in the diagnosis information storage unit 103, and the feature in the diagnosis record information (see FIG. 10) stored in the report analysis unit 105. The features are respectively "gland ducts" and "signet ring cells". Therefore, the comparing unit 116 determines that the features do not match with each other, and sets the matching score to be −1. The result is transmitted to the caution display unit 107.

The caution display unit 107 displays a caution indicating that the features used in pathological diagnosis do not match with each other (in Step S603), and the flow is ended as it is (in Step S607). Further, the caution display unit 107 displays that the features do not match with each other along with the features and the attribute information thereof (in Step S606).

According to the second exemplary embodiment of the present invention, it is possible to prevent a deviation between a diagnosis result on a tissue specimen image and the contents of a report created by a pathologist, and to evaluate the detailed reasons in addition to a pathological diagnosis result.

Third Exemplary Embodiment

In the third exemplary embodiment, comparison is made between diagnosis record information described in a report stored in a report storage unit 104, and diagnosis record information stored in a diagnosis information storage unit 103 for determining a degree of matching between both of the diagnosis record information. A difference from the second exemplary embodiment is that a plurality of diagnosis record information is stored in the diagnosis information storage unit 103.

The extracting method and the comparing method of pieces of tissue specimen identification information (IDs), and a region of interest (ROI) recorded in the diagnosis information storage unit 103 and in a report analysis unit 105 are the same as in the first exemplary embodiment, and accordingly, description thereof is omitted herein (in Steps S600 and S601).

In the following, a flow of comparing between features and between attribute information thereof is described referring to FIGS. 9A to 9C and FIG. 10, when a plurality of diagnosis result information is recorded in the diagnosis information storage unit 103.

It is assumed that a pathological report stored in a report storage unit 104 describes "gland ducts of different sizes are crowded". Features and attribute information thereof are extracted by the same method as in the first exemplary embodiment, and accordingly, description thereof is omitted herein. In the case of the present exemplary embodiment, the extracted features are "gland ducts", and the extracted attribute information is "sizes are different from each other" and "crowded".

It is assumed that there are three cases (see FIG. 9A, FIG. 9B, and FIG. 9C) as illustrated in FIGS. 9A to 9C, in which the pathological specimen identification information (ID) match with each other, and the regions of interest (ROI) match with each other in the pathological report (see FIG. 10) recorded in the diagnosis information storage unit 103 and stored in the report storage unit 104. In this case, comparison is made between the features and between the attribute information thereof described in the pathological report for each of the related diagnosis record information (in Step S602).

<When Features, and Attribute Information of Features Match with Each Other>

A comparing unit 116 of a report verification unit 106 compares a region of interest 1 recorded in the diagnosis information storage unit 103, and a feature or features and attribute information thereof described in the pathological report (in Step S602). First of all, the comparing unit 116 compares between the feature in the diagnosis record information (see FIG. 9A) stored in the diagnosis information storage unit 103, and the feature in the diagnosis record information (see FIG. 10) stored in the report analysis unit 105. In the case of the present exemplary embodiment, both of the features are "gland ducts". Therefore, the comparing unit 116 determines that the features match with each other, and sets the matching score to be +1.

Subsequently, the comparing unit 116 compares between attribute information of the feature. The diagnosis information storage unit 103 stores the information (see FIG. 9A) indicating "density: 70%", and the report analysis unit 105 stores the information (see FIG. 10) indicating "crowded". The comparing unit 116 determines that both of the attribute information match with each other with use of the same method as applied in the second exemplary embodiment.

Subsequently, the comparing unit 116 compares the information relating to the size of the feature. The diagnosis information storage unit 103 stores the information indicating "there is a size variation". The report analysis unit 105 stores the information (see FIG. 10) indicating "sizes are different from each other". Also in this case, the comparing unit 116 determines that both of the information match with each other with use of the same method as applied in the second exemplary embodiment.

The item "sizes are different from each other" about gland ducts has a weighting value +7, and the item "crowded" about gland ducts has a weighting value +5, from the information recorded in a feature-based importance degree table recording unit 126.

A score calculating unit 136 calculates a caution score with use of the matching score and the weighting values obtained as described above (in Step S604). The caution score calculating method is the same as applied in the second exemplary embodiment, and accordingly, description thereof is omitted herein.

<When Features, and Attribute Information of Features do not Match with Each Other>

The comparing unit 116 compares between the feature in the diagnosis record information (see FIG. 9B) stored in the diagnosis information storage unit 103, and the feature in the diagnosis record information (see FIG. 10) stored in the report analysis unit 105. In the case of the present exemplary embodiment, the features are different from each other. Therefore, the comparing unit 116 determines that the features do not match with each other, and sets the matching score to be −1.

When −1 is provided as the matching score on features, a caution score is not calculated any more. A state that the matching score is −1 means that the feature included in the diagnosis record information stored in the diagnosis information storage unit 103 is new information that has not been described in the pathological report.

A caution display unit 107 displays that the features do not match with each other along with the calculated caution score, the features, and the attribute information thereof. In this case, the caution display unit 107 may display these information pieces in the ascending order of the value of the matching degree.

The comparing unit 116 compares between the feature in the diagnosis record information (see FIG. 9C) stored in the diagnosis information storage unit 103, and the feature in the diagnosis record information (see FIG. 10) stored in the report analysis unit 105. This method is the same as the aforementioned method for comparing between the diagnosis record information (see FIG. 9B) stored in the diagnosis information storage unit 103, and the diagnosis record information (see FIG. 10) stored in the report analysis unit 105. Therefore, description of the method is omitted herein.

As described above, according to the third exemplary embodiment of the present invention, it is possible to prevent a deviation between a diagnosis result on a tissue specimen image and the contents of a report created by a pathologist, and to evaluate the detailed reasons in addition to a pathological diagnosis result.

As described above, the present invention has been described referring to the exemplary embodiments. The present invention, however, is not limited to the above-mentioned exemplary embodiments. Various modifications comprehensible to a person skilled in the art can be made to the configuration and the details of the present invention within the scope of the invention of the present application.

This application is based upon and claims the benefit of priority from Japanese Patent Application No. 2012-118726, filed on May 24, 2012, the disclosure of which is incorporated herein in its entirety by reference.

REFERENCE SIGNS LIST

101 Image storage unit
102 Diagnosis unit
103 Diagnosis information storage unit
104 Report storage unit
105 Report analysis unit
106 Report verification unit
107 Caution display unit
112 Diagnosis feature recognition unit
122 Diagnosis feature analysis unit
132 Diagnosis recording unit
115 Extracting unit
125 Recording unit
116 Comparing unit
126 Feature-based importance degree table recording unit
136 Score calculating unit

The invention claimed is:

1. A pathological diagnosis results assessment system, comprising:
at least one storage device that includes at least report storage and diagnosis record storage;
at least one processor connected to the at least one storage device;
a memory storing instructions that, upon execution by the at least one processor, cause the at least one processor to:
perform a pathological diagnosis of a tissue specimen image, that includes extracting a region of interest, a name of a feature, and attribute information of the feature, for generating diagnosis record information, and attribute information of the feature, and storing the diagnosis record information in the diagnosis record storage of the at least one storage device;
store a report describing a pathological diagnosis result on the tissue specimen image in the report storage of the at least one storage device;
analyze the diagnosis result described in the report stored in the report storage, the analysis including extracting, from the stored report, the region of interest, the name of the feature, and the attribute information of the feature, to obtain a diagnosis result; and
compare the obtained diagnosis result to the diagnosis record information stored in the diagnosis record storage of the at least one storage device, and determine a degree of matching on the diagnosis degree of the comparison result, including comparing the region of interest, the name of the feature, and the attribute information of the feature extracted from the stored report, with pieces of the diagnosis record information in the diagnosis record storage, setting a matching score by matching of the name of the feature, and calculating a caution score with use of the matching score, and a predetermined weighting value for each of the name of the feature and the attribute information of the feature, wherein the weighting value is set in accordance with the feature and the attribute information of the feature.

2. The pathological diagnosis results assessment system according to claim 1, wherein
the pathological diagnosis extracts a plurality of regions of interest, and
the comparing of the diagnosis result to the diagnosis record information includes comparing the diagnosis record information for each of the plurality of the regions of interest, and calculating the caution score with use of the set matching score.

3. The pathological diagnosis results assessment system according to claim 2, wherein execution of the instructions further cause the processor to display features that match with each other, in addition to features that do not match with each other in the order of the caution score.

4. The pathological diagnosis results assessment system according to claim 1, wherein the diagnosis unit extracts a plurality of regions of interest, and
the report verification unit compares the diagnosis record information for each of the plurality of the regions of interest, and calculates the caution score with use of the set matching score.

5. A pathological diagnosis results assessment method executed on a system comprising at least one storage device that includes at least report storage and diagnosis record storage, at least one processor, and a memory storing instructions, that upon execution, cause the at least one processor to perform the method comprising:
performing a pathological diagnosis of a tissue specimen image, that includes extracting a region of interest, a name of a feature, and attribute information of the feature, for generating diagnosis record information, storing the diagnosis record information in a diagnosis record storage of the at least one storage device;
storing a report describing a pathological diagnosis result on the tissue specimen image in the report storage of the at least one storage device;
analyzing the diagnosis result described in the report stored in the report storage of the at least one storage device, the analysis including extracting, from the stored report, the region of interest, the name of the feature, and the attribute information of the feature, to obtain a diagnosis result;
comparing the diagnosis result analyzed in the report analyzing step to the diagnosis record information stored in the diagnosis record storage of the at least one storage device, and determining a degree of matching on the diagnosis degree of the comparison result, including comparing the region of interest, the name of the feature, and the attribute information of the feature extracted from the stored report, with pieces of the diagnosis record information in the diagnosis record storage, setting a matching score by matching of the name of the feature, and calculating a caution score with use of the matching score, and a predetermined weighting value for each of the name of the feature and the attribute information of the feature, wherein the weighting value is set in accordance with the feature and the attribute information of the feature.

6. The pathological diagnosis results assessment method according to claim 5, wherein in the diagnosing, a plurality of regions of interest are extracted, and in the verifying, the diagnosis record information is compared for each of the plurality of the regions of interest, and the caution score is calculated with use of the set matching score.

7. The pathological diagnosis results assessment method according to claim 6, further comprising:

a caution display step of displaying features that match with each other, in addition to features that do not match with each other in the order of the caution score.

8. The pathological diagnosis results assessment method according to claim 5, wherein in the diagnosing, a plurality of regions of interest are extracted, and in the verifying, the diagnosis record information is compared for each of the plurality of the regions of interest, and the caution score is calculated with use of the set matching score.

9. A pathological diagnosis results assessment device, comprising:

at least one processor that connects to a storage device that includes at least report storage and diagnosis record storage;

a memory storing instructions that, upon execution by the at least one processor, cause the at least one processor to:

perform a pathological diagnosis of a tissue specimen image, that includes extracting a region of interest, a name of a feature, and attribute information of the feature, for generating diagnosis record information, and attribute information of the feature, and storing the diagnosis record information in the diagnosis record storage of the storage device;

store a report describing a pathological diagnosis result on the tissue specimen image in the report storage of the storage device;

analyze the diagnosis result described in the report stored in the report storage, the analysis including extracting, from the stored report, the region of interest, the name of the feature, and the attribute information of the feature, to obtain a diagnosis result; and compare the obtained diagnosis result to the diagnosis record information stored in the diagnosis record storage of the storage device, and determining a degree of matching on the diagnosis degree of the comparison result, including comparing the region of interest, the name of the feature, and the attribute information of the feature extracted from the stored report, with pieces of the diagnosis record information in the diagnosis record storage, setting a matching score by matching of the name of the feature, and calculating a caution score with use of the matching score, and a predetermined weighting value for each of the name of the feature and the attribute information of the feature, wherein the weighting value is set in accordance with the feature and the attribute information of the feature.

10. The pathological diagnosis results assessment device according to claim 9, wherein the pathological diagnosis extracts a plurality of regions of interest, and the comparing of the diagnosis result to the diagnosis record information includes comparing the diagnosis record information for each of the plurality of the regions of interest, and calculating the caution score with use of the set matching score.

11. The pathological diagnosis results assessment device according to claim 10, wherein execution of the instructions further cause the processor to display features that match with each other, in addition to features that do not match with each other in the order of the caution score.

12. The pathological diagnosis results assessment device according to claim 9, wherein the diagnosis unit extracts a plurality of regions of interest, and the report verification unit compares the diagnosis record information for each of the plurality of the regions of interest, and to calculate the caution score with use of the set matching score.

* * * * *